(12) United States Patent
Ho

(10) Patent No.: US 8,689,366 B2
(45) Date of Patent: Apr. 8, 2014

(54) MASK ATTACHMENT ASSEMBLY

(75) Inventor: Peter Chi Fai Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 131 days.

(21) Appl. No.: 12/976,254

(22) Filed: Dec. 22, 2010

(65) Prior Publication Data

US 2011/0088700 A1 Apr. 21, 2011

Related U.S. Application Data

(63) Continuation of application No. 11/485,778, filed on Jul. 13, 2006, now Pat. No. 7,877,817.

(60) Provisional application No. 60/699,705, filed on Jul. 15, 2005.

(51) Int. Cl.
*A61F 9/02* (2006.01)

(52) U.S. Cl.
USPC .............................. 2/452; 128/207.11; 2/6.2

(58) Field of Classification Search
USPC .............. 2/6.2, 6.3, 448, 450, 452, 302, 308, 2/311, 318, 319, 323, 341; 128/206.11–206.13
See application file for complete search history.

(56) References Cited

U.S. PATENT DOCUMENTS

| | | | |
|---|---|---|---|
| 3,013,556 A | 12/1961 | Galleher | |
| 5,429,126 A | 7/1995 | Bracken | |
| 5,517,986 A * | 5/1996 | Starr et al. | 128/206.24 |
| 5,542,128 A * | 8/1996 | Lomas | 2/173 |
| 5,884,624 A | 3/1999 | Barnett | |
| 6,038,706 A * | 3/2000 | Seiler | 2/426 |
| 6,341,383 B1 | 1/2002 | Beltrani | |
| 6,397,847 B1 | 6/2002 | Scarberry | |
| 6,494,207 B1 | 12/2002 | Kwok | |
| 6,516,802 B2 | 2/2003 | Hansen | |
| 6,662,803 B2 | 12/2003 | Gradon | |
| 6,805,117 B1 | 10/2004 | Ho | |
| 6,931,664 B1 | 8/2005 | Chen | |
| 2002/0117177 A1 | 8/2002 | Kwok | |
| 2002/0144336 A1 | 10/2002 | Montague | |
| 2004/0045551 A1 | 3/2004 | Eaton | |
| 2004/0067333 A1 * | 4/2004 | Amarasinghe | 428/99 |

* cited by examiner

*Primary Examiner* — Katherine Moran
(74) *Attorney, Agent, or Firm* — Michael W. Haas

(57) ABSTRACT

A strap for use in a mask attachment assembly. The strap includes a hook pad provided on a first portion of a surface of the strap located and having a first width extending perpendicularly to a longitudinal axis of the strap. The hook pad includes a plurality of hooks. Loops are provided on a second portion of the surface of the strap. The second portion has a second width extending perpendicularly to the longitudinal axis of the strap. The plurality of loops extend entirely across the second width and are configured to engage the plurality of hooks in a releasable and engageable manner. The second width is greater than the first width, and an outer edge portion of the first portion of the surface surrounding at least a portion of the hook pad, wherein the outer edge portion does not include any hooks.

8 Claims, 16 Drawing Sheets

MASK ATTACHMENT ASSEMBLY

CROSS-REFERENCE TO RELATED APPLICATIONS

This application is a Continuation application under 35 U.S.C. §120 of U.S. patent application Ser. No. 11/485,778 filed Jul. 13, 2006, now U.S. Pat. No. 7,877,817, which claims priority under 35 U.S.C. §119(e) from provisional U.S. patent application Ser. No. 60/699,705 filed Jul. 15, 2005 the contents of which are incorporated herein by reference.

BACKGROUND OF THE INVENTION

1. Field of the Invention

The present invention relates generally to structures and assemblies for use in connection with a patient interface device, such as a respiratory mask, and a mask attachment assembly, such as a headgear having straps to retain the mask in a sealed position on a user's face and, in particular, to a mask attachment assembly for connection to the respiratory mask and providing attachable and releasable straps, thereby providing additional convenience, ease-of-use, ease-of-adjustment and removal and improved comfort to the patient.

2. Description of the Related Art

It is well known to treat a medical disorder or to diagnose, treat or monitor the condition of the patient using medical equipment. For example, a patient may be monitored and treated for various sleep disorders in a lab or in some other setting. An example of a type of sleep disorder is sleep apnea. Obstructive sleep apnea is characterized by a collapse of the upper airways during sleep, while central sleep apnea is characterized by the suspension of all respiratory movement. Obstructive sleep apnea and central sleep apnea may be combined in a condition referred to as mixed apnea.

In order to diagnose and/or treat such medical disorders, various equipment and devices are required for successful diagnosis and a resulting prescribed treatment. Further, there are numerous situations where it is necessary or desirable to deliver a flow of breathing gas, non-invasively, to the airway of a patient, i.e., without intubating the patient or surgically inserting a tracheotomy tube in their trachea. For example, it is known to ventilate a patient using a technique known as non-invasive ventilation. It is also known to deliver continuous positive airway pressure (CPAP) or variable airway pressure, which varies with the patient's respiratory cycle or a monitored condition of the patient, to treat a medical disorder, such as sleep apnea syndrome, in particular, obstructive sleep apnea (OSA), congestive heart failure, stroke, Cheynes-Stokes respiration, etc. Non-invasive ventilation and pressure support therapies involve the placement of a patient interface device, which is typically a nasal or nasal/oral mask, on the face of a patient to interface the ventilator or pressure support device with the airway of the patient, so that a flow of breathing gas can be delivered from the pressure/flow generating device to the airway of the patient.

Patients suffering from a pulmonary or respiratory disorder, such as obstructive sleep apnea, are often treated with a pressure support device, such as a continuous positive airway pressure (CPAP) device. A CPAP device delivers a flow of fluid to the airway of the patient throughout the patient's breathing cycle in order to "splint" the airway open, thereby preventing its collapse during sleep. In another type of treatment, bi-level positive pressure therapy is provided to the patient, in which the pressure of air delivered to the patient's airway varies or is synchronized with the patient's breathing cycle to maximize therapeutic effect and comfort to the patient. A pressure support device may also provide "bi-level" pressure support, in which a lower pressure is delivered to the patient during the patient's expiratory phase then during the inspiratory phase.

It is also known to provide an auto-titration positive pressure therapy in which the pressure provided to the patient changes based upon the detected conditions of the patient, such as whether the patient is snoring or experiencing an apnea, hypopnea, or upper airway resistance. Such a device adjusts the pressure delivered to the patient, based on whether or not the patient is snoring. For example, a pressure support device may actively test the patient's airway to determine whether obstruction, complete or partial, could occur and adjust the pressure output to avoid this result.

Other modes of providing positive pressure support to a patient are known. For example, a proportional assist ventilation mode of pressure support provides a positive pressure therapy in which the pressure of gas delivered to the patient varies with the patient's breathing effort to increase the comfort of the patient. Proportional positive airway pressure (PPAP) devices deliver breathing gas to the patient based on the flow generated by the patient.

For purposes of the present invention, the phrase "pressure support system", "pressure support device", or "positive pressure support" includes any medical device or method that delivers a flow of breathing gas to the airway of a patient, including a ventilator, CPAP, bi-level, PAV, PPAP, or bi-level pressure support system.

Typically, gas such as oxygen or air is delivered by a pressure generating device, which may be, in turn, in fluid communication with an oxygen tank. The oxygen flows from the source through the regulator devices, through the pressure generating device and further through a conduit into a patient interface. The pressure generating device and the conduit, such as a gas hose, are considered the patient circuit, such that a coupling assembly is required for connecting the patient circuit to the patient interface device.

In a conventional pressure support system, a flexible conduit is coupled to an exit conduit from the pressure generating device. The flexible conduit forms part of the patient circuit that carries the flow of breathing gas from the pressure generating system to the patient interface device. In a support system, the patient interface device connects the patient circuit with the airway of the patient so that the elevated pressure gas flow is delivered to the patient's airway.

In order to provide gas or, as discussed above, oxygen to a patient, the patient must use a patient interface device, such as a nasal mask (including external cushions and/or internal prongs), nasal/oral mask, full-face mask, nasal cannula, oral mouthpiece, tracheal tube, endotracheal tube, or hood. Typically, patient interface devices include a mask shell having a cushion attached to the shell that contacts the surface of the patient. The mask shell and cushion are held in place by a headgear that wraps around the head of the patient. Together, the mask and headgear form the patient interface assembly. A typical mask attachment assembly includes headgear having flexible, adjustable straps that extend from the mask to attach the mask to the patient. Other techniques for attaching a patient interface device use a vice-like device that anchors at the front and back of the patient's head to support the mask on the user. See, e.g., U.S. Pat. No. 6,516,802.

Because such patient interface devices are typically worn for an extended period of time, a variety of concerns must be taken into consideration. For example, in providing CPAP or other positive pressure therapy to treat OSA, the patient normally wears the patient interface device all night long while he or she sleeps. In order to be successful in these applications, a patient interface device needs to consider two, often competing, goals: comfort and technical effectiveness. Failure to achieve either goal is likely to result in low efficacy. A comfortable, but technically ineffective, patient interface device may achieve superior patient compliance; however, its technical ineffectiveness will minimize the therapeutic benefit achieved. Alternatively, a technically effective, but uncomfortable, patient interface may be capable of treating a patient; yet, the lack of comfort often results in low patient compliance. Low patient compliance also undermines the therapeutic benefit ultimately obtained by the patient. Thus, further advancements for interfacing a pressure support system to the airway of a patient are desired.

It is known to maintain such interface devices on the face of a wearer by a headgear having upper and lower straps, each having opposite ends threaded through connecting elements provided on the opposite sides and top of the interface device, such as a mask. Because such masks are typically worn for an extended period of time, it is important that the headgear maintain the mask tight enough to seal against a patient's face without discomfort. Adjustability of the mask and/or the headgear, together with increased patient comfort, is paramount. However, most important is the maintenance of the seal between the mask and the user's face. According to the prior art, various headgear have been developed that position the straps in various locations with respect to the mask in order to effect this seal.

According to the prior art, a variety of mask attachment assemblies, headgear, straps and the like are disclosed and used for maintaining engagement between the mask and the user's face. For example, one such a headgear is discussed in U.S. Pat. No. 6,662,803 to Graden et al. As best illustrated in FIG. 2 of the Graden patent, a mask is held against the user's face using a headgear, which is secured around the back of the user's head. The positioning and use of multiple straps of the headgear in connection with the mask and the forehead member provide the compressive force to effect the required seal.

Another prior art headgear assembly is disclosed in U.S. Pat. No. 6,805,117 to Ho et al. This reference teaches an adjustable headgear with a front adjustment strap attached to a portion of a headpiece and extending past each side of the headpiece, which defines front adjustment strap portions. A rear joint piece is attached to a central portion of the rear edge portion at an upper edge, such that the rear joint piece is positionable along the lower portion of the patient's head. Rear adjustment straps are attached to upper tabs, and each rear adjustment strap is further attached to a portion of the rear edge of the headpiece. The front adjustment straps and rear adjustment straps include some fastening system for adjustably and releasably connecting the strap end portions to each other. In this manner, an adjustable headgear is provided that fits and can be adjusted to fit differently sized patients.

Another such headgear is disclosed in U.S. Pat. No. 5,517,986 to Starr et al. In particular, the headgear of the Starr patent includes a headpiece adapted to fit the crown and back of a patient's head. As seen in FIG. 1 of the Starr patent, lower straps provide a two-point connection with a gas delivery mask. Depending straps depending from headpiece are connected to and moveable relative to the lower straps. Additionally, a pair of upper straps and can be used to provide a four-point connection with the gas delivery mask, if needed, as shown in FIG. 7 of the Starr patent.

While all of the above-referenced prior art headgear and mask attachment assemblies provide some adjustability and flexible positioning of the headgear or assembly, there is considerable room in the art for improved adjustability. Such additional and beneficial characteristics would allow the mask to fit a wider variety of patients, and would greatly improve the comfort provided to the patient wearing the headgear for an extended period of time. In addition, effective and quick attachment and detachment of the headgear or assembly, which engages and disengages the mask, provides a much more functional and user-friendly device.

SUMMARY OF THE INVENTION

Accordingly, it is an object of the present invention to provide a strap for use in a mask attachment assembly that addresses one or more of the above-identified concerns and overcomes the shortcomings of conventional mask mounting assemblies, masks, headgear and the like in the gas delivery art. In accordance with the broad teachings of the present invention, a strap for use in a mask attachment assembly and a mask attachment assembly using such strap is provided. The strap includes a hook pad provided on a first portion of a surface of the strap located and having a first width extending perpendicularly to a longitudinal axis of the strap. The hook pad includes a plurality of hooks. Loops are provided on a second portion of the surface of the strap. The second portion has a second width extending perpendicularly to the longitudinal axis of the strap. The plurality of loops extend entirely across the second width and are configured to engage the plurality of hooks in a releasable and engageable manner. The second width is greater than the first width, and an outer edge portion of the first portion of the surface surrounding at least a portion of the hook pad, wherein the outer edge portion does not include any hooks.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION OF THE EXEMPLARY EMBODIMENTS

Figure 1:
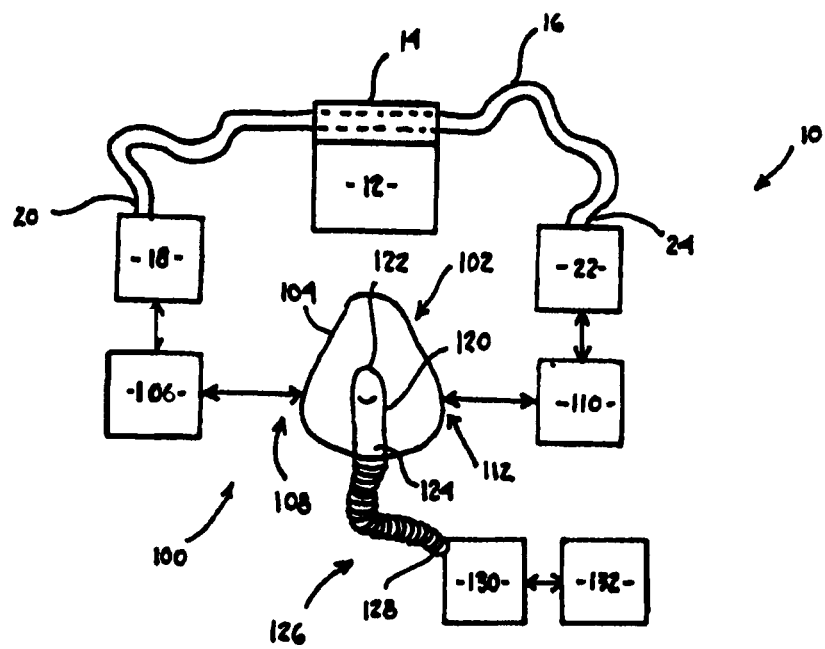
FIG. 1 is a schematic view of a mask mounting assembly and patient interface device according to the principles of the present invention.

The present invention is directed to a mask attachment assembly 10 as illustrated in various embodiments in FIGS. 1-13, and to a patent interface device 100, as illustrated in various embodiments in FIGS. 1-6. In particular, and as illustrated in schematic form in FIGS. 1 and 2, the mask attachment assembly 10 is designed to be used in connection with the patient interface device 100. The patient interface device 100 includes a mask 102, and this mask 102 can be a nasal mask (including an external cushion and/or internal prongs), an oral mask, a nasal and oral mask, a full-face mask or other similar devices and structures as are known in the art. In addition, the mask attachment assembly 10 of the present invention can be used in connection with any of the components and subcomponents of the patient interface device 100. The mask 102 includes a mask port (not shown) extending through a mask wall 104. In operation, the mask port allows gas, such as oxygen, air and the like, to flow through the mask port and into the mask 102 for inhalation by the patient.

The present invention is also directed to the patient interface device 100 that includes the mask attachment assembly 10 as described herein. In one embodiment, the patient interface device 100 includes a mask conduit coupling 120 in fluid communication with the mask port (not shown). In a further embodiment, the mask conduit coupling 120 includes a first end 122 and a second end 124. The first end 122 of the mask conduit coupling 120 is attached to the mask 102, and the second end 124 of the mask conduit coupling 120 is in fluid communication with a patient circuit 126, a conduit 128, a pressure support device 130, a gas source 132 or any combination thereof. The patient circuit 126 is an arrangement that is known in the art. In particular, the patient circuit 126 typically includes the conduit 128 in fluid communication with the pressure support device 130. In operation, the gas, typically oxygen or air, flows from the pressure support device 130, which may receive oxygen from an oxygen tank or other similar gas source 132, through the conduit 128, further through the mask conduit coupling 120 and the mask port and into the mask 102, as discussed above. In this manner, the patient receives gas delivery for inhalation.

Figure 2:
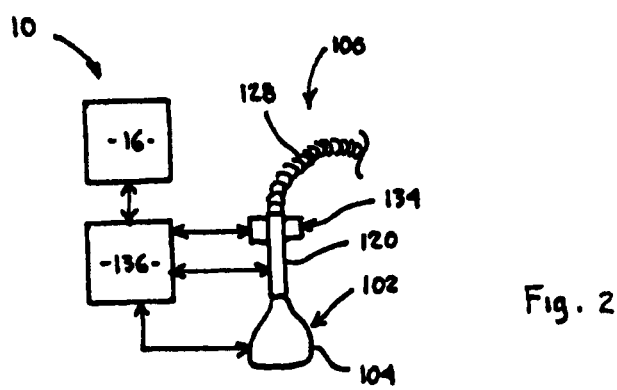
FIG. 2 is a schematic view of a mask attachment assembly and patient interface device according to the principles of the present invention.

As shown in FIG. 2, the patient interface device 100 may include a forehead support assembly 134, which includes a forehead contact member attached to and extending from the mask 102. An example of one type of forehead support assembly is shown and described in U.S. Publication No. 2004/0045551, which has been assigned to the Assignee of the present invention and incorporated herein by reference. At least a portion of the forehead contact member contacts a portion of a user's forehead. As is known in the art, the forehead contact member may include a padded element for comfortably contacting the user's forehead. For example, the padded element can be a gel-filled cushion, such as a detachable gel-filled cushion, which is shown and described in U.S. Pat. Nos. 5,884,624 and 6,397,847, which have been assigned to the Assignee of the present invention and incorporated herein by reference.

Also as shown in FIG. 2, an engagement member 136 may be directly or indirectly attached to the mask conduit coupling 120, the forehead support assembly 134 or any combination thereof, and this engagement member 136 is adapted to engage an attachment mechanism, member or assembly of the mask attachment assembly 10 of the present invention. For example, the engagement member 136 may be in the form of a buckle, a buckle with a release slot (as discussed hereinafter), or any other attachment device or mechanism as is known in the art, and which is capable of engaging with the mask attachment assembly 10.

With respect to the present invention, the mask attachment assembly 10 includes a panel member 12 with one or more sleeves 14 extending along a portion of the panel member 12. In addition, the assembly 10 includes at least one, and typically multiple, straps 16 extending through and slidable within a respective sleeve 14. The strap 16 includes a first attachment assembly 18 positioned on a first end 20 of the strap 16. This first attachment assembly 18 is configured to engage a first engagement member 106 positioned on a first side 108 of the mask 102. In addition, the strap 16 includes a second attachment assembly 22 positioned on a second end 24 of the strap 16. Similarly, the second attachment assembly 22 is configured or adapted to engage a second engagement member 110 positioned on a second side 112 of the mask 102.

In operation, and in order to adjust the mask attachment assembly 10, the strap 16 is repositionable by releasing the first attachment assembly 18 and/or the second attachment assembly 22 from the respective engagement member 106, 110. Next, the strap 16 is slid through the sleeve 14 of the panel member 12. In addition, the panel member 12 can be slid or adjusted with respect to the straps 16, thereby allowing appropriate repositioning on the back of the user's head. Finally, the first attachment assembly 18 and/or the second attachment assembly 22 is re-engaged with the respective engagement member 106, 110. In this manner, the user may reposition the straps 16 and/or the panel member 12 in a variety of positions to improve comfort and flexibility of attachment.

Figure 3:
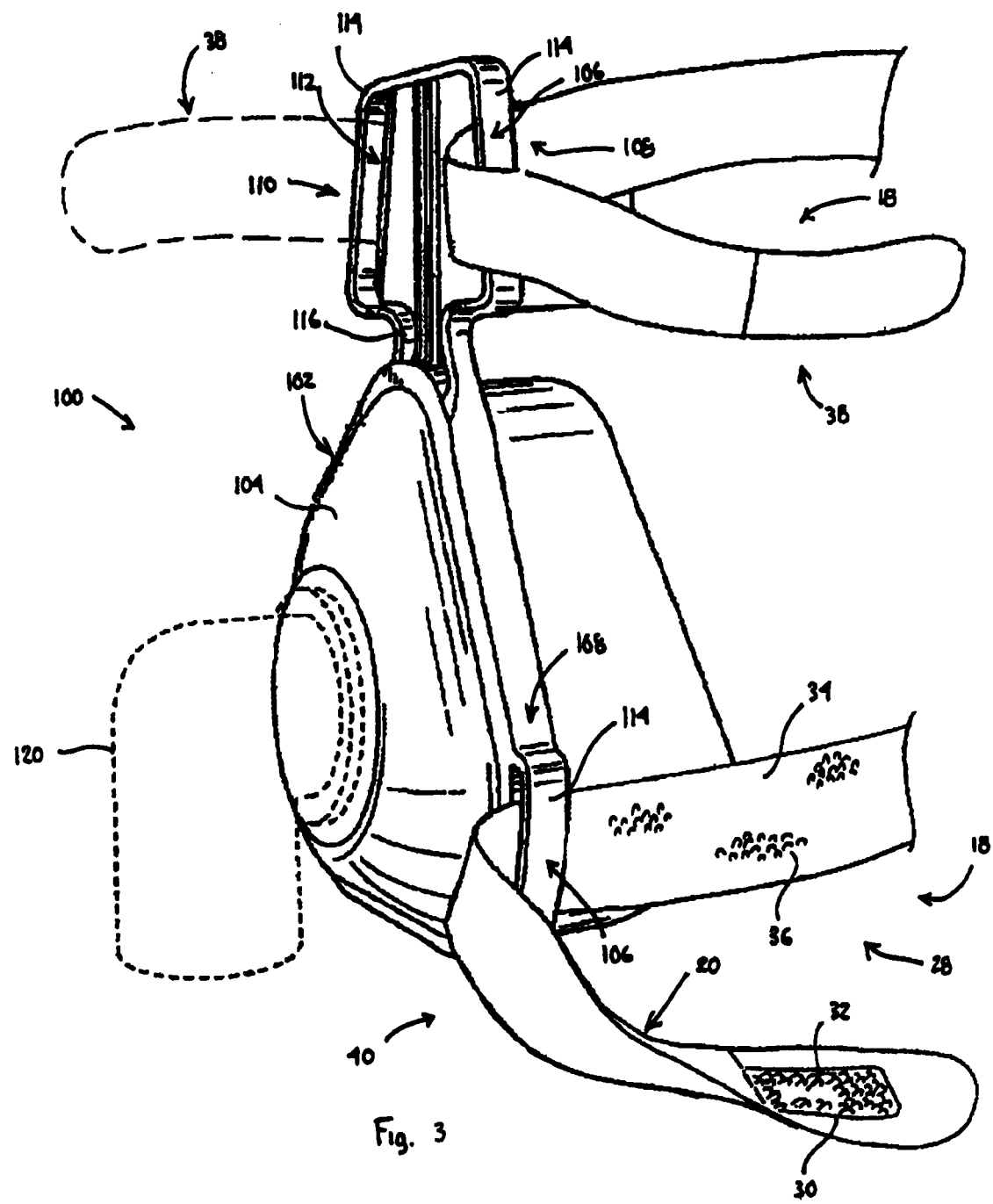
FIG. 3 is a perspective view of one embodiment of a mask mounting assembly and patient interface device according to the principles of the present invention.
Figure 4:
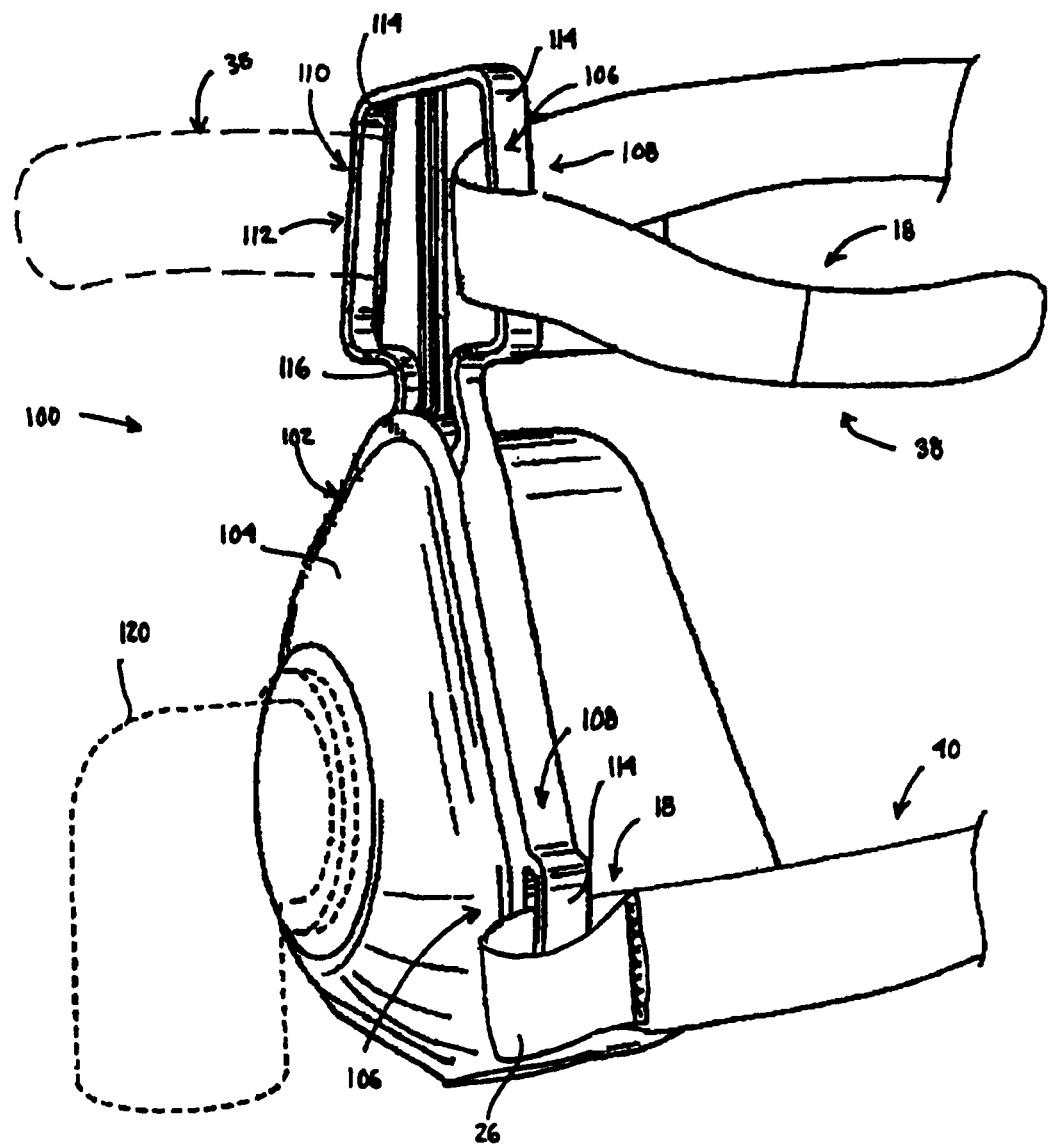
FIG. 4 is a perspective view of a further embodiment of a mask mounting assembly and patient interface device according to the principles of the present invention.

As seen in FIGS. 3 and 4, the first engagement member 106 and/or the second engagement member 110 may be in the form of a buckle 114, which is directly or indirectly attached to the mask 102 or some other component or subcomponent of the patient interface device 100, such as the mask conduit coupling 120, the forehead support assembly 134, etc. This buckle 114 is adapted to engage the first attachment assembly 18 and/or the second attachment assembly 22 of the mask attachment assembly 10. As seen in the embodiment of FIGS. 3 and 4, four buckles 114 are provided. In particular, a buckle 114 is attached to or integrally formed with the mask wall 104 on the first side 108 of the mask 102, as well as the second side 112 of the mask 102. In addition, in this embodiment, two additional buckles 114 are provided on an extension member 116, which is attached to, integrally formed with and/or extends from the mask wall 104. Each buckle 114 is sized and shaped so as to engage and interact with a strap 16, and in particular the first attachment assembly 18 and/or the second attachment assembly 22 of each strap 16.

The extension member 116 may take many forms. In particular, in one embodiment, the extension member extends outwardly from the mask towards the user's chin and lip area a given distance. In another embodiment, the extension member extends toward the user's forehead in an upward direction and a similar distance. In either embodiment, in this orientation, the extension member 116 minimizes the potential for contact between the user's face and the attachment assemblies 18, 22 of the mask mounting assembly 10. Another unique aspect of this extension member 116 is that by extending outwardly from the mask, the extension member creates an extended lever between mask 102 and straps 16. By extending outwardly, the torque, or moment, applied by the extension member 116 is increased for a given applied force. One skilled in the art can best appreciate that the torque, or moment, applied may be adjusted by either increasing or decreasing the length of the extension member 116 as desired.

Figure 5:
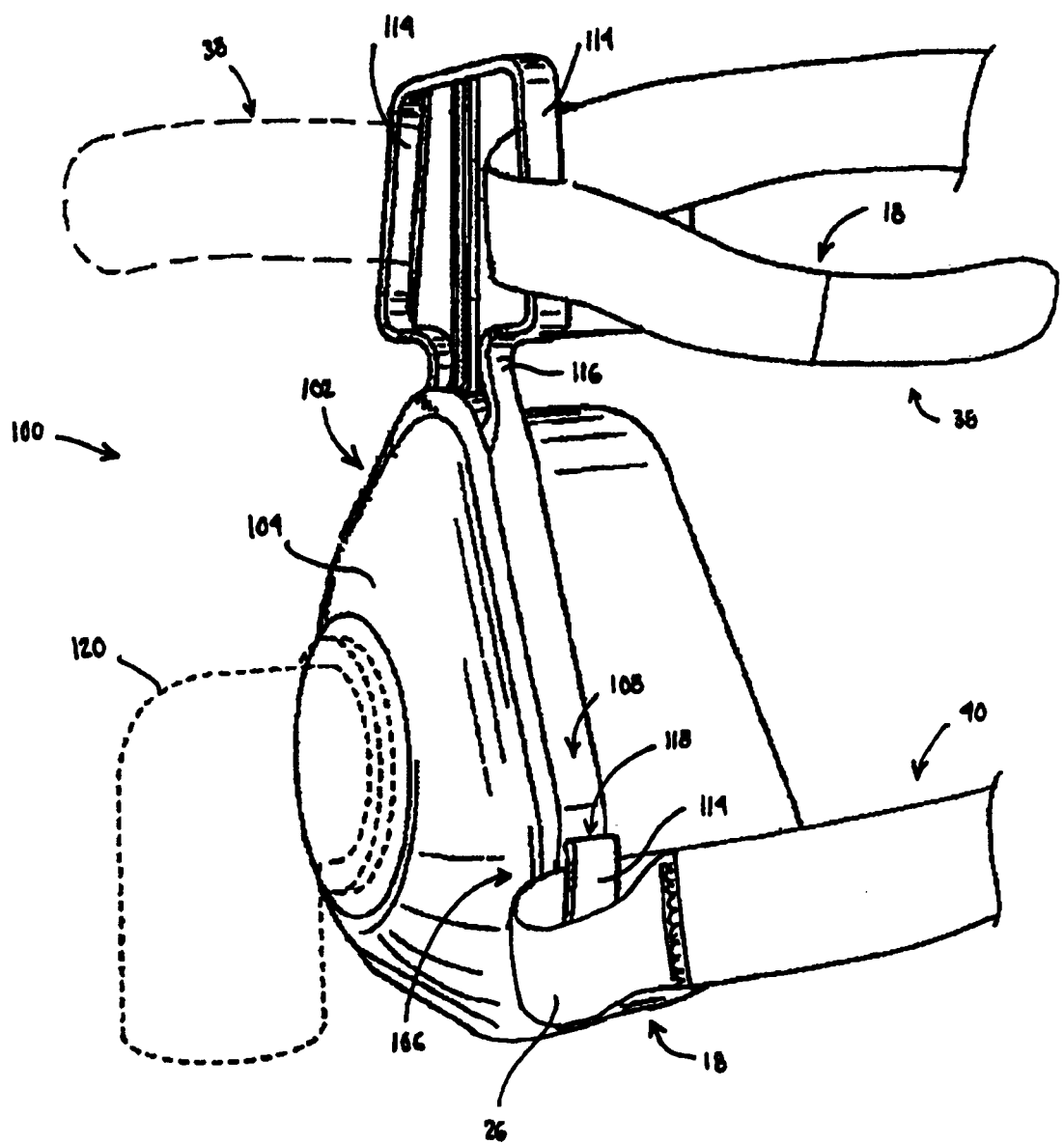
FIG. 5 is a perspective view of a still further embodiment of a mask mounting assembly and patient interface device according to the principles of the present invention.

In a further embodiment illustrated in FIG. 5, at least one of the buckles 114 includes a release slot 118. Such a release slot 118 allows the user to quickly engage and release the first attachment assembly 18 and/or second attachment assembly 22 from the mask 102. Accordingly, regardless of the means and structure of the attachment assembly 18, 22, the attachment assembly 18, 22, as well as the strap 16, is easily removed through the release slot 118. Accordingly, if the patient feels the urge to quickly remove the mask 102, he or she does not need to engage or disengage any of the components, instead simply moving the straps 16 through the release slot 118, and thereby quickly removing the mask 102. In addition, the patient would not need to readjust the straps 16 for reattachment, instead simply re-engaging the attachment assembly 18, 22 of the strap 16 through the release slot 118 and back into engagement with the buckle 114.

In one embodiment, the first attachment assembly 18 and/or the second attachment assembly 22 are permanently engaged with the respective engagement member 106, 110. Further, in this embodiment, the other attachment assembly 18, 22 (that is, the attachment assembly 18, 22 that is not permanently engaged) is releasably engaged with the respective engagement member 106, 110. Therefore, even while one of the attachment assemblies 18, 22 is permanently engaged with the mask 102, the use of the releasable attachment assembly 18, 22 in connection with the strap 16, which slides through the sleeve 14, allows the user to adjust the mask attachment assembly 10 to attain his or her desired positions.

In one embodiment, and as seen in FIGS. 4 and 5, the permanently engaged attachment assembly 18, 22 is a loop 26. In particular, the loop 26 is attached to the engagement member, which in this embodiment is the buckle 114 with the release slot 118. The loop 26 is formed by attaching or otherwise joining an end portion of the strap 16 in order to form this loop 26. For example, the loop 26 can be formed by sewing an end of the strap 16 to a middle portion of the strap 16, as would be readily apparent to one skilled in the art. In operation, even though the loop 26 is permanently attached to the buckle 114, it may still be quickly removed through the release slot 118. Of course, it is also envisioned that the loop 26 is permanently formed around a buckle 114 that does not include the release slot 118. Such an embodiment is illustrated in FIG. 4. In this embodiment, the release and adjustment occurs at the releasable attachment assembly 18, 22, as the loop 26 would not be removable from the buckle 114 without the release slot 118.

As seen in FIG. 3, the releasably engaged attachment assembly 18, 22 may be a hook-and-loop structure 28, which, when engaged, forms a releasable contact structure. Such a temporary engagement-type hook-and-loop structure 28 is known in the art. In one preferred embodiment, the hook-and-loop structure 28 includes at least one, and typically multiple, hook pads 30, where each hook pad 30 includes multiple hooks 32. In this embodiment, the hook pads 30 are attached to a strap surface 34. In addition, the strap surface 34 is covered with or formed with multiple loops 36 that are configured to engage the hooks 32 of the hook pad 30. In this manner, a releasable hook-and-loop structure 28 is provided, where the hook pads 30 are releasably engageable with the loops 36 and the strap surface 34 of the strap 16.

As discussed above, multiple hook pads 30 may be used, and these hook pads 30 can be spaced along the strap surface 34. This provides multiple releasable loop positions and configurations of the strap 16. Accordingly, the user or patient can be provided with further adjustment possibilities and a variety of positions for the mask attachment assembly 10.

Figure 6:
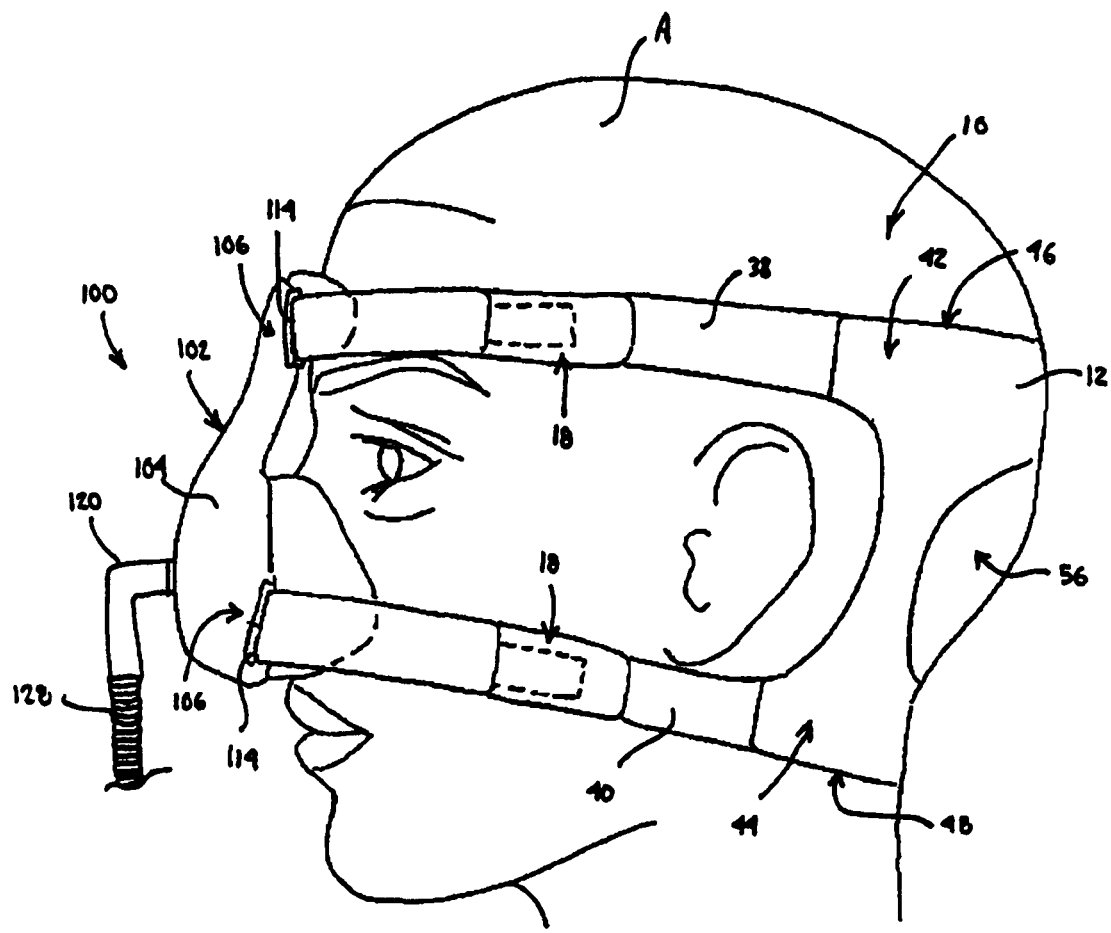
FIG. 6 is a perspective view of a mask mounting assembly and patient interface device according to the principles of the present invention in use by a patient.

The mask attachment assembly 10, and the patient interface device 100, of the present invention are illustrated in use in FIG. 6. As seen in this embodiment, multiple straps 16 are used, and each strap 16 extends through and is slidable within a respective sleeve 14, which extends along a respective portion of the panel member 12. Therefore, in one preferred embodiment, two straps are used, namely a top strap 38 and a bottom strap 40, and the top strap 38 extends through a top sleeve 42, while the bottom strap 40 extends through a bottom sleeve 44.

Figure 7:
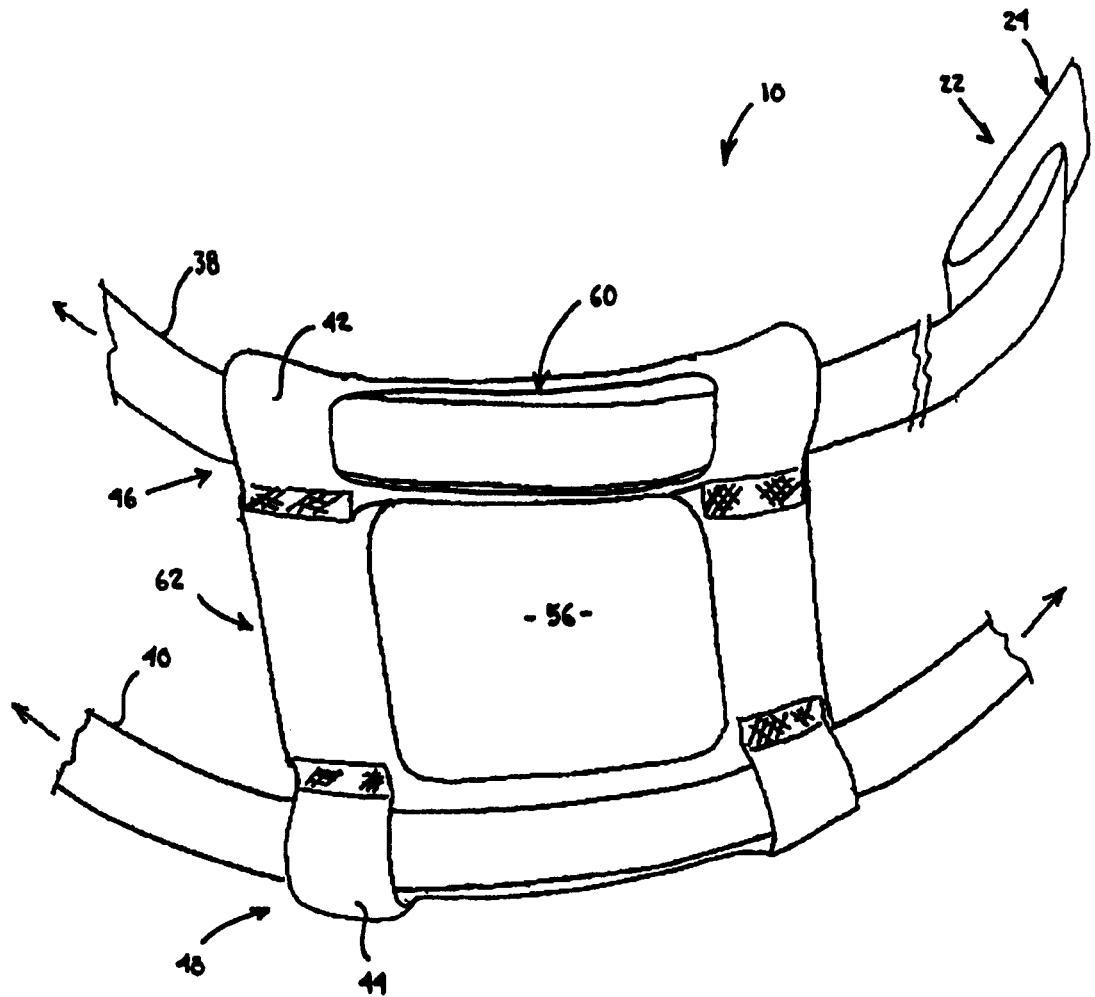
FIG. 7 is a perspective view of one embodiment of a mask mounting assembly according to the principles of the present invention.

As best seen in FIG. 7, the top sleeve 42 is formed at an upper portion 46 of the panel member 12. Similarly, the bottom sleeve 44 extends along and is formed in a lower portion 48 of the panel member 12. As seen in the embodiment of FIG. 7, the sleeves 42, 44 can be formed by attaching, such as by sewing, an edge of the panel member 12 against a middle portion of the panel member 12. In this manner, and as is known in the art, such a sleeve 14 would be formed for use in engaging with a respective strap 16. Further, the sleeves 14 are sized and shaped so as to slidably receive the strap 16 so that the user can slide the strap 16 and reposition the panel member 12 on the user's head A. In addition, the sleeves 14 may be formed by a plurality of spaced loops, such as seen in the embodiments of FIGS. 9-13. These spaced and aligned individual loops form and operate as the sleeve 14.

The panel member 12 includes a contact surface 50. For example, see FIGS. 8 and 9. This contact surface 50 directly contacts at least a portion of the patient's head A in use. Therefore, the comfort of the contact surface 50 is of utmost importance. In this regard, at least a portion of the contact surface 50 may be formed from a specific material that would feel comfortable to a patient in use. In addition, the contact surface 50 may include a textured surface or some coating layer (or any combination thereof) for modifying the feeling of the contact surface 50 when touching the patient's head A.

Figure 8:
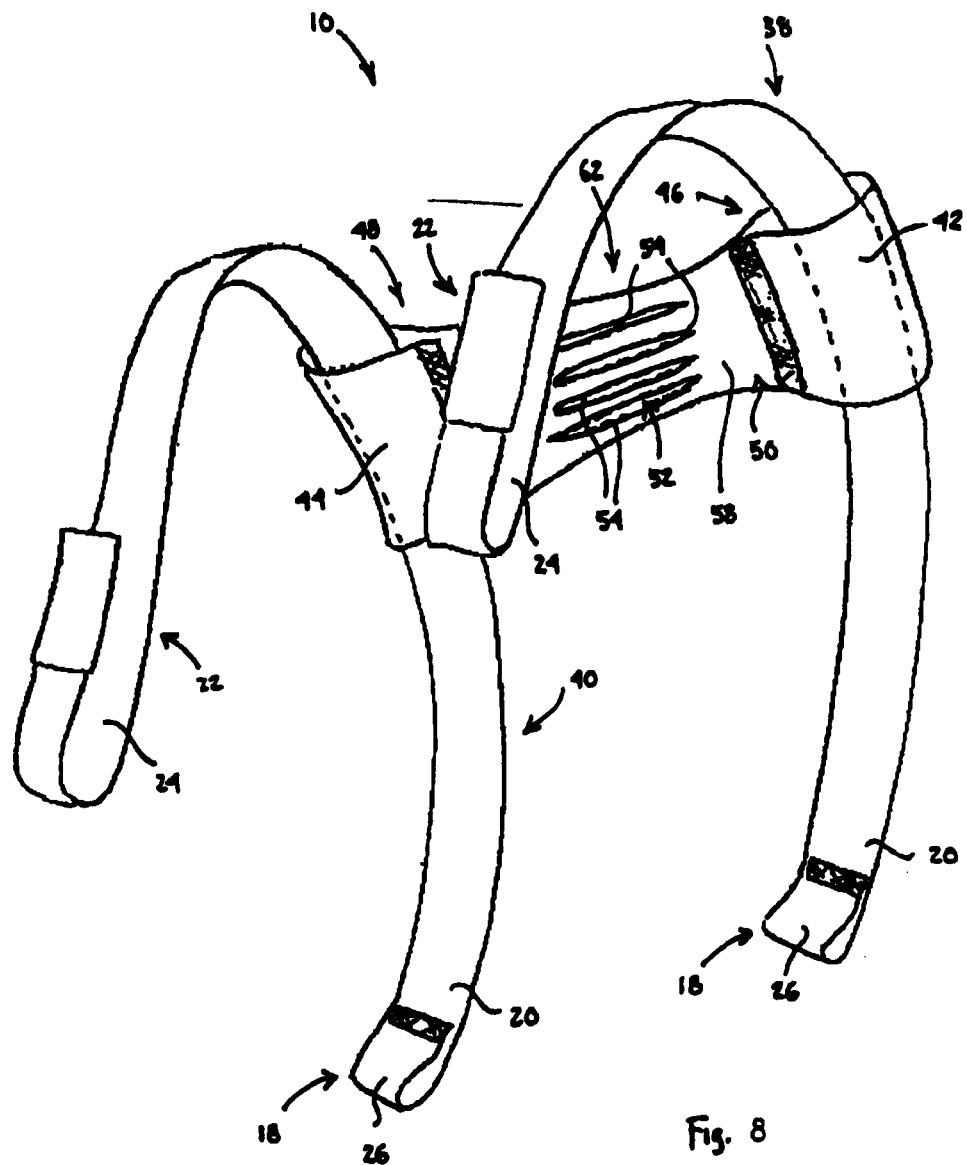
FIG. 8 is a perspective view of another embodiment of a mask mounting assembly according to the principles of the present invention.

For example, a textured surface 52 is illustrated in FIG. 8. In this embodiment, the textured surface 52 includes a plurality of ribs 54 attached to, extending from and/or integrally formed with the contact surface 50 of the panel member 12. For example, these ribs 54 could modify the gripping characteristics of the contact surface 50, and could also be padded and provide a more comfortable contact surface 50. A variety of textured surfaces 52 is envisioned, and such a textured surface 52 could modify not only the feeling of the contact surface 50, but also other characteristics, such as the aforementioned gripping characteristics, of the contact surface 50.

In the embodiment of FIG. 8, a top strap 38 and a bottom strap 40 are used and, in this embodiment, the first attachment assembly 18 of each of the straps 38, 40 is releasable using the above-discussed hook-and-loop structure 28, while the second attachment assemblies 22 of each of the straps 38, 40 are permanently attachable to or engageable with the buckle 114. For example, in this embodiment, a loop 26 is used as the second attachment assembly 22 for each strap 38, 40 and is either permanently engaged with the buckle 114 or engageable and disengageable through the use of the release slot 118 on the buckle 114.

As seen in each of the embodiments of FIGS. 7 and 9-13, the contact surface 50 may include a cutout 56 extending through the panel member 12, and specifically this cutout 56 extends through a wall 58 of the contact surface 50. Such a cutout 56 would allow the user's head A to "breathe" or otherwise allow air circulation when the mask attachment assembly 10 is used. For example, without such a cutout 56 in the contact surface 50, it may grow hot or otherwise uncomfortable at the back of the user's head A during extended periods of use of the mask attachment assembly 10. Still further, the cutout 56 allows the contact surface 50 to better and more comfortably conform to the back of the user's head A. The cutout 56 may be sized and shaped so as to provide a secure grip between the contact surface 50 and the back of the user's head A.

Also as seen in FIG. 7, a cutout 60 may be formed in the sleeve 14 of the panel member 12. This cutout 60 would be used to allow the user to better manipulate and move the straps 16 through the respective sleeve 14 during the adjustment process. Of course, as seen in connection with the lower portion 48 of the panel member 12 in the embodiment of FIG. 7, a cutout 60 would not be required if the sleeve 14 was simply formed by attaching a portion of the panel member 12 to itself and forming multiple spaced and aligned loops, which comprise the above-discussed sleeve 14.

Figure 9:
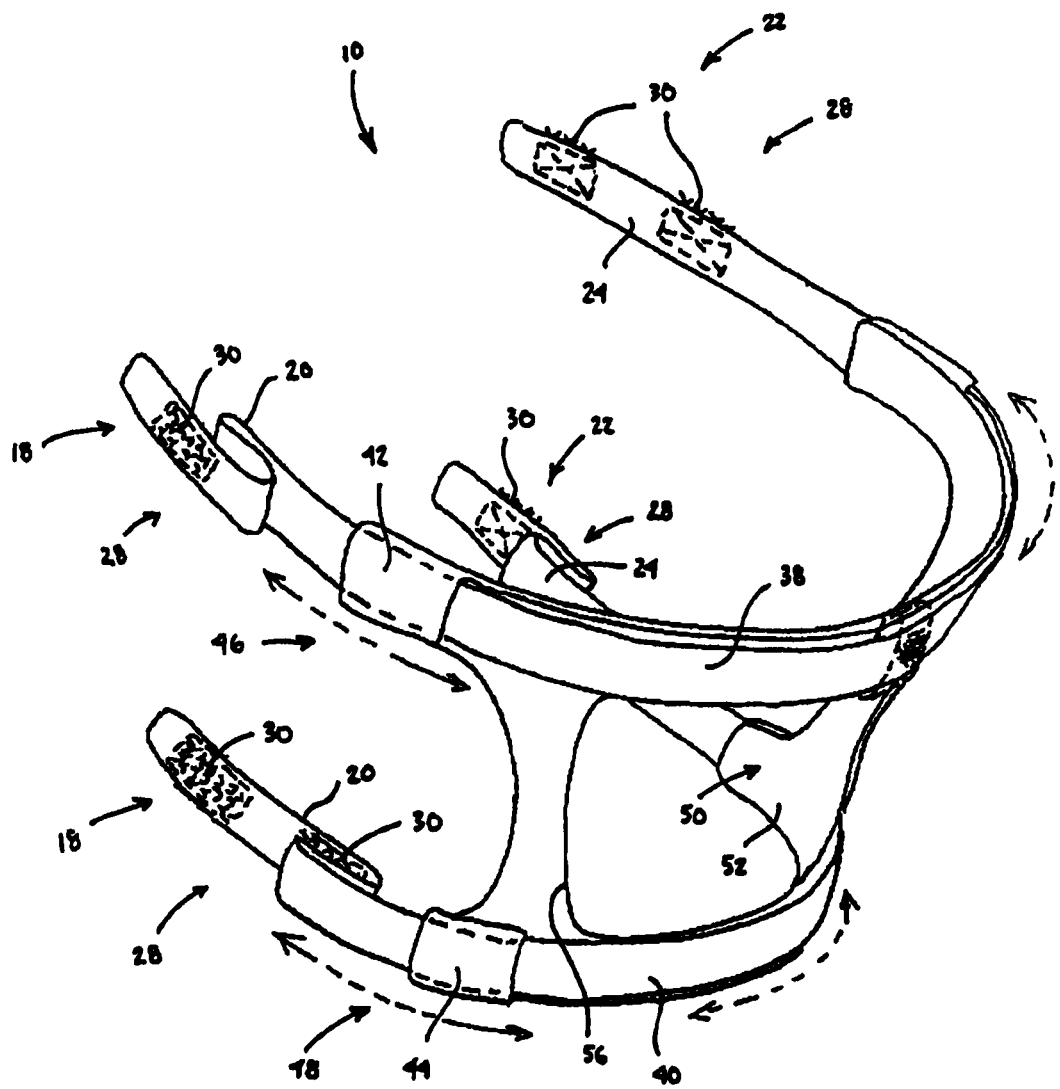
FIG. 9 is a perspective view of a further embodiment of a mask mounting assembly according to the principles of the present invention.

As illustrated in FIG. 9, any number of configurations can be created. In this embodiment, multiple pads 30 are attached to or formed with straps 16. In particular, two hook pads 30 are attached to the first end 20 of each strap 38, 40, while two hook pads 30 are also attached to the second end 24 of each strap 38, 40. Therefore, both the first end 20 and second end 24 of each strap 38, 40 are releasably engageable with the respective engagement member 106, 110 of the mask 102. Further, each strap 38, 40 is slidable within and along the top sleeve 42 and the bottom sleeve 44. The embodiment of FIG. 9 also provides a large cutout 56 in the panel member 12.

In order to provide still further adjustability and flexibility of positioning of the mask attachment assembly 10 of the present invention, multiple sleeves 14 can be positioned adjacent each other on the upper portion 46 of the panel member 12, the lower portion 48 of the panel member 12 or any combination thereof. Each of these stacked sleeves 14 may slidingly receive a strap 16, and this overall structure provides lateral adjustment positions for the strap 16 when engaged with a respective sleeve 14. This allows the user to adjust the positions of the straps 16, panel member 12 and even the seal characteristics of the mask 102 with respect to the user's head A, through the use of this lateral adjustment feature. In addition, such adjustment allows the mask attachment assembly 10 to be used in connection with various head sizes.

Figure 10:
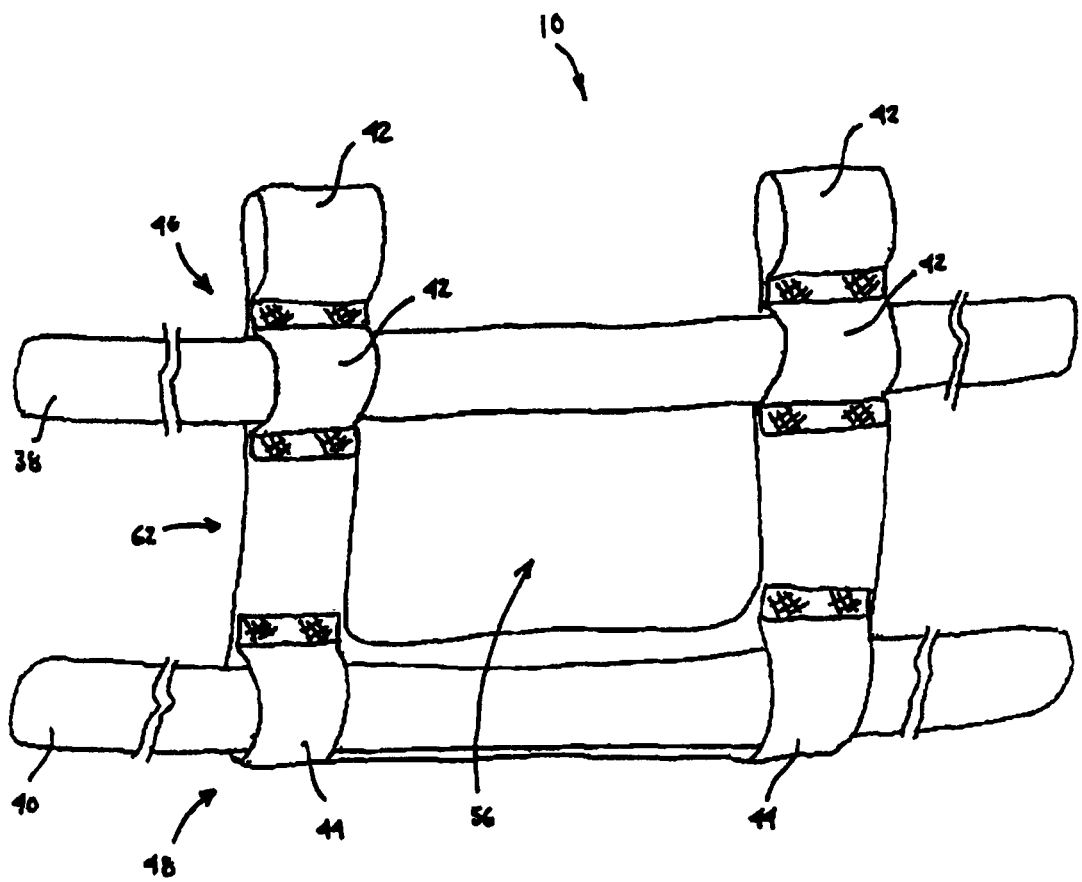
FIG. 10 is a perspective view of another embodiment of a mask mounting assembly according to the principles of the present invention.

In the embodiment of FIG. 10, two top sleeves 42 are provided on the upper portion 46 of the panel member 12. A single bottom sleeve 44 is provided on the lower portion 48 of the panel member 12. In addition, the cutout 56 is created by the lower portion 48 of the panel member 12, and the top strap 38. In use, the patient may remove the top strap 38 and use it in any one of the top sleeves 42 of the panel member 12.

Figure 11:
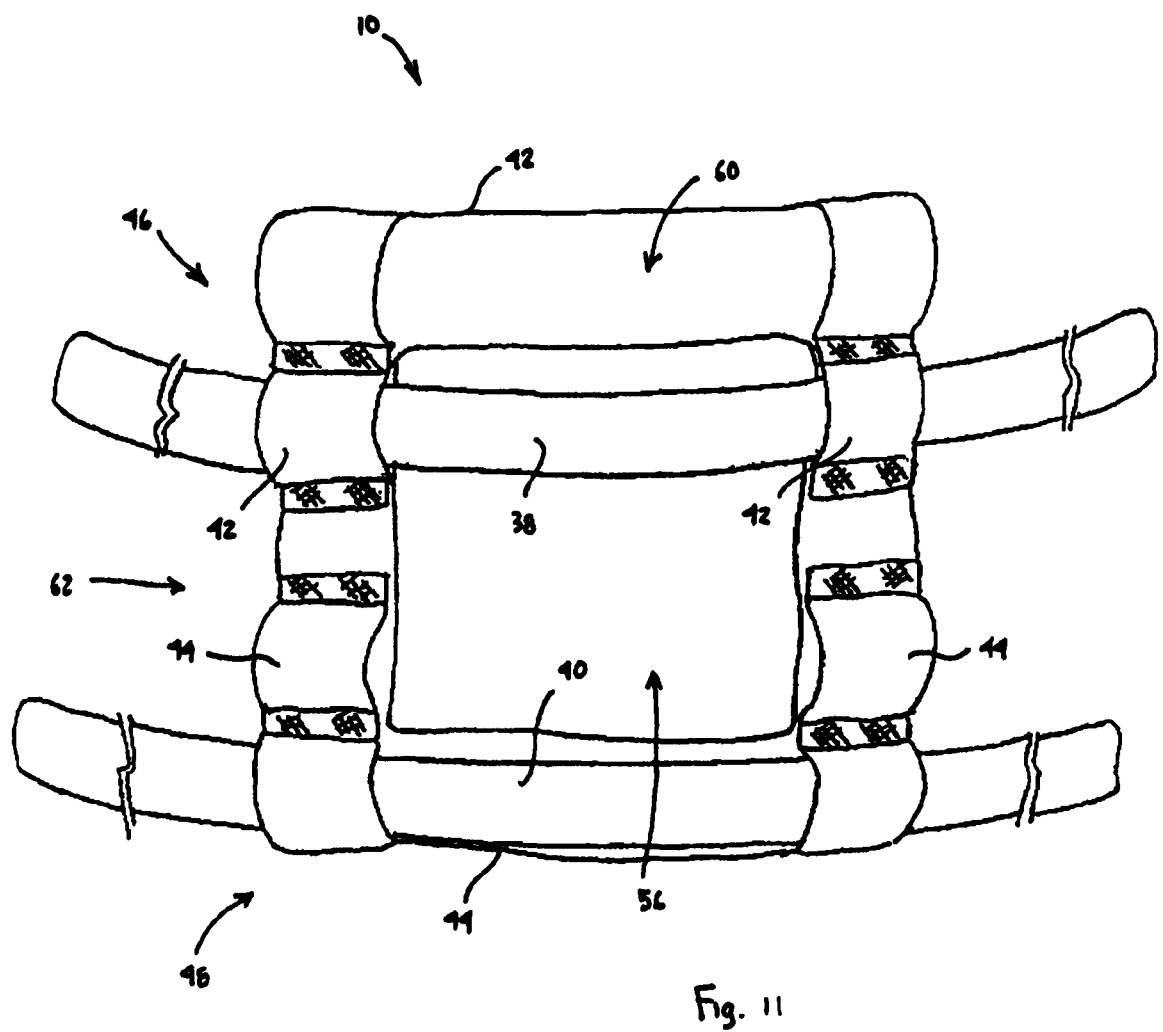
FIG. 11 is a perspective view of a still further embodiment of a mask mounting assembly according to the principles of the present invention.

As seen in the embodiment of FIG. 11, both the upper portion 46 and the lower portion 48 of the panel member 12 include multiple, stacked sleeves 14. In particular, this embodiment includes two top sleeves 42 on the upper portion 46 of the panel member 12, and two bottom sleeves 44 on the lower portion 48 of the panel member 12. As discussed above, this provides the user with further flexibility and the ability to laterally position the straps 38, 40 for additional comfort and functionality.

Figure 12:
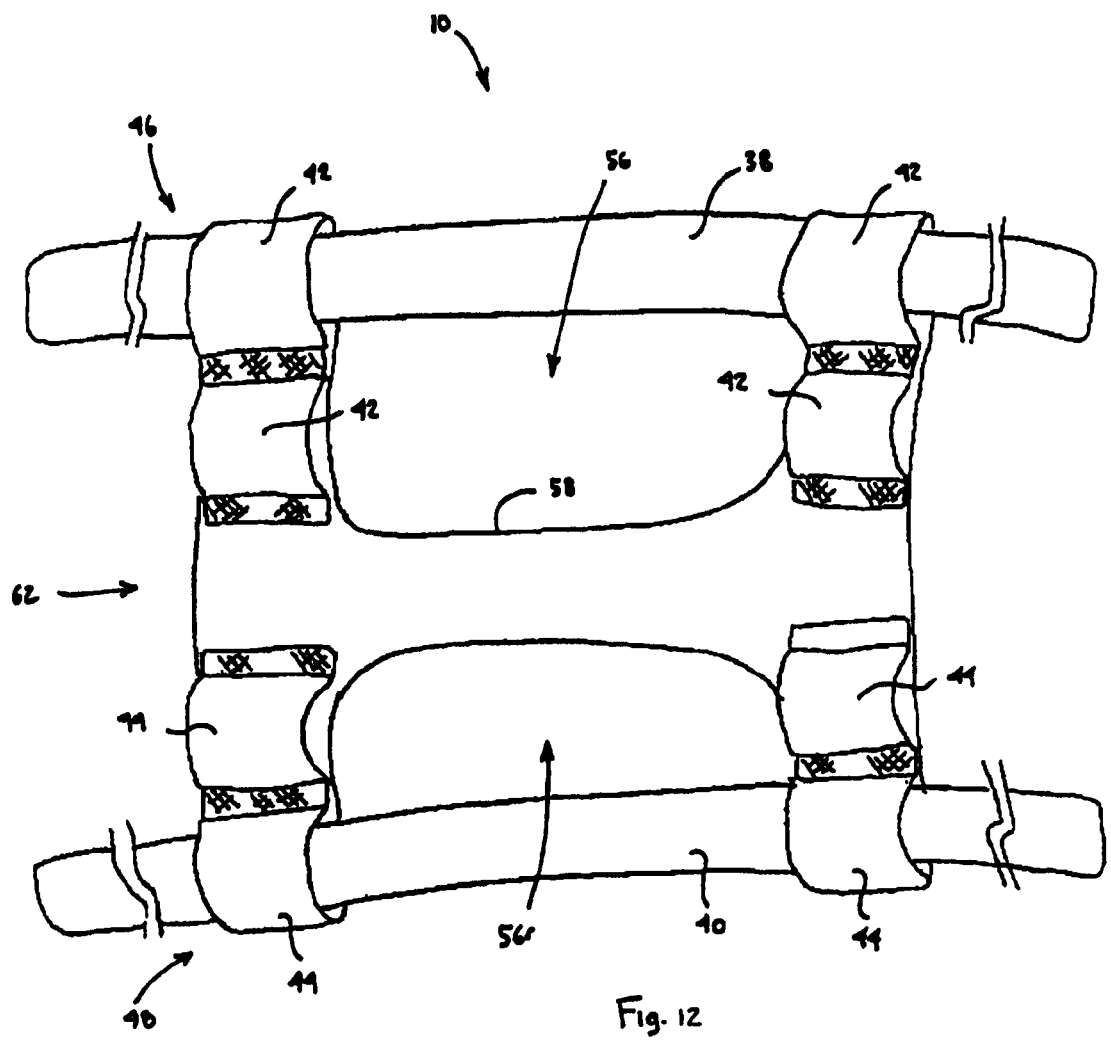
FIG. 12 is a perspective view of another embodiment of a mask mounting assembly according to the principles of the present invention.

In the embodiment of FIG. 12, multiple cutouts 56 surround the contact surface 50. In particular, the cutouts 56 are formed by a center portion 62 of the panel member 12, together with the top strap 38 and the bottom strap 40. This embodiment illustrates yet another configuration for providing the variable position function to the user.

Figure 13:
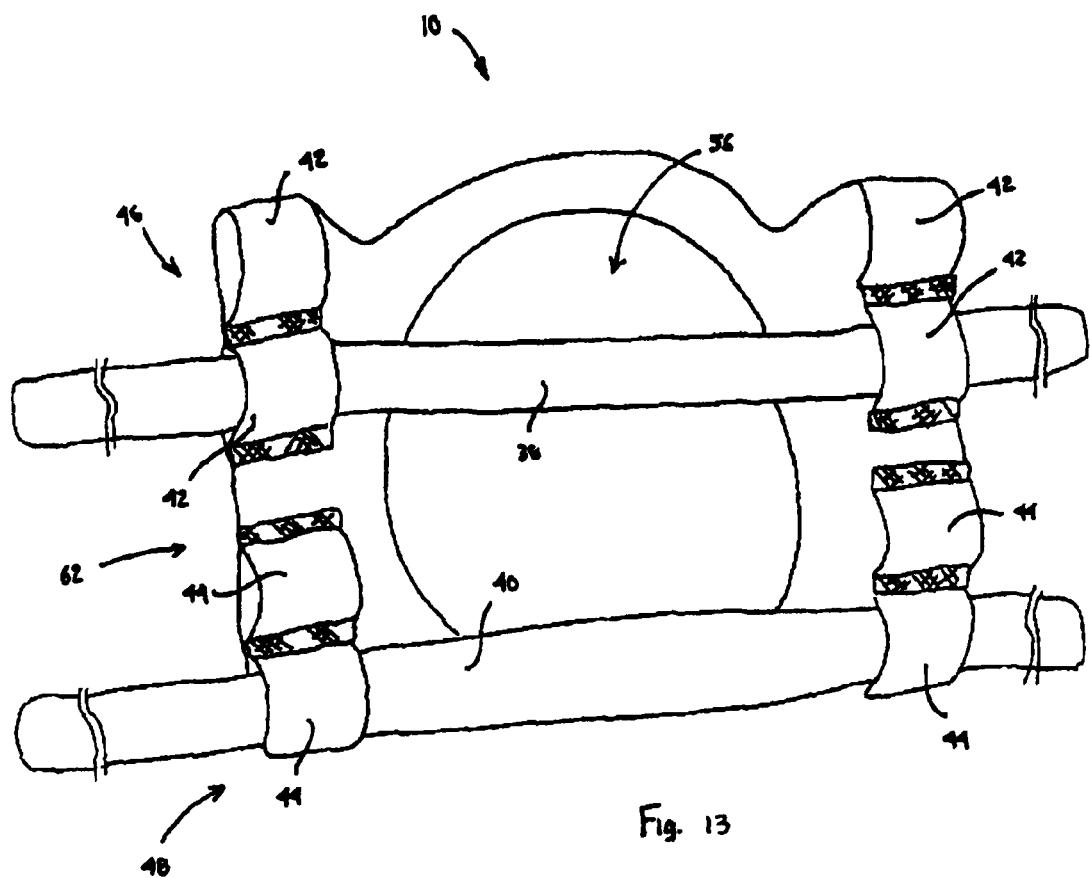
FIG. 13 is a perspective view of yet another embodiment of a mask mounting assembly according to the principles of the present invention.

In yet another embodiment, and as illustrated in FIG. 13, the panel member 12 includes a semicircular shape, and the cutout 56 is a circular shape extending through the wall 58 of the contact surface 50. The use of such a circular shape allows the panel member 12 to better conform to the user's head A in use. In particular, due to the generally rounded surface of the back of the user's head A, the use of the circular cutout 56 provides better and more uniform contact of the contact surface 50 with the user's head A, which also results in a better mask 102 seal. Further, in this embodiment, two top sleeves 42 and two bottom sleeves 44 are provided for lateral positioning of the top strap 38 and bottom strap 40.

Figure 14:
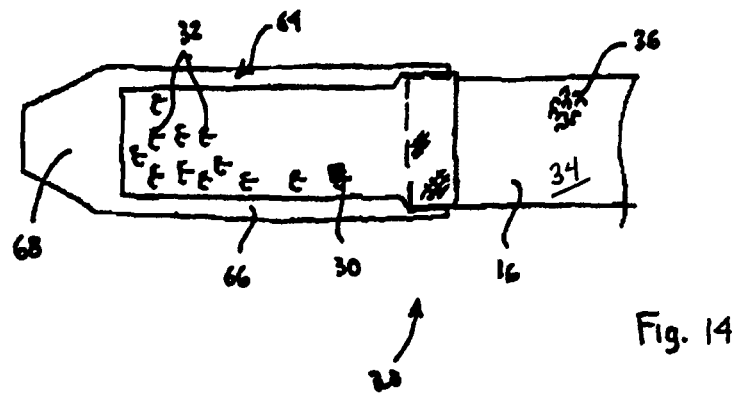
FIG. 14 is a plan view of a strap and attachment assembly for use in a mask mounting assembly according to the principles of the present invention.
Figure 15:
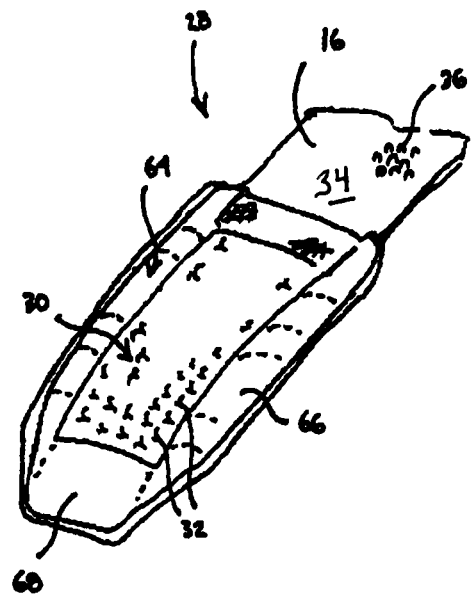
FIG. 15 is a perspective view of the strap of FIG. 14.

The present invention is also directed to a novel hook-and-loop structure 28 for use in connection with the strap 16, which is illustrated in various embodiments in FIGS. 14-21. This hook-and-loop structure 28 includes hook pad 30, which includes multiple hooks 32 extending therefrom. Further, in this embodiment, the surface 34 of the strap 16 includes—multiple loops 36 for engaging the hooks 32. However, according to the present invention, an edge surface 64 extends around the hook pad 30. Further, this edge surface 64 is formed from a coated material, a soft material, a padded material, a pliable material or any combination thereof. As seen in the embodiment of FIGS. 14 and 15, the edge surface 64 is in the form of a padded rim 66. Further, the edge surface 64 includes a release tab 68 positioned adjacent the hook pad 30 and at the end 20, 24 of the strap 16.

In use, the presently-invented hook-and-loop structure 28 with the novel edge surface 64 is beneficial since oftentimes the user quickly attaches the strap 16. According to the prior art, the edge of the hook pad would extend beyond the boundary of the strap and the hooks or hook pad edge would contact and rub against the user's head, providing a great deal of discomfort. However, according to the present invention, the beneficial edge surface 64, whether coated or made from a soft or pliable material, would cause no discomfort if quickly placed and extending beyond the boundary of the strap 16. For example, the padded rim 66 would cause no discomfort to the user if extending beyond the edge of the strap 16 and against the user's head A. Further, the release tab 68 could be used to quickly remove the strap 16 and, therefore, the mask 102. Still further, in the embodiment of FIGS. 14 and 15, the hook pad 30 is overlapped with and attached to the strap 16. In particular, in this embodiment, the hook pad 30 is sewn to the strap 16.

Figure 16:
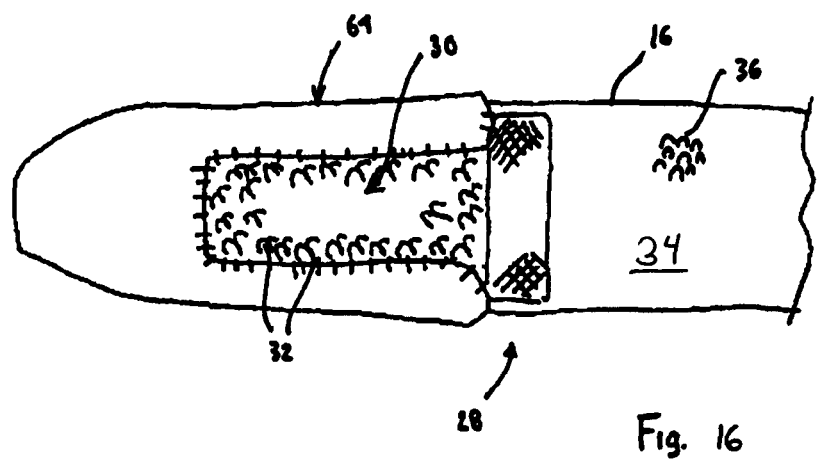
FIG. 16 is a plan view of another embodiment of a strap and attachment assembly for use in a mask mounting assembly according to the principles of the present invention.
Figure 17:
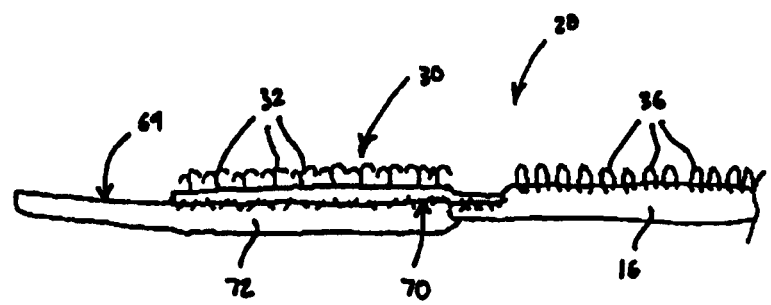
FIG. 17 is a side view of the strap and attachment assembly of FIG. 16.

As seen in the embodiment of FIGS. 16 and 17, the hook pad 30, and specifically a bottom portion 70 of the hook pad 30, is sewn against the strap surface 34. Further, the bottom portion 70 of the hook pad 30 is sewn against an end piece 72. Specifically, this end piece 72 extends beyond the boundary of the hook pad 30 and forms the beneficial edge surface 64, such as the padded rim 66. Accordingly, the embodiment of FIGS. 16 and 17 provides a three-piece structure, wherein the hook pad 30 is sewn or attached to the strap 16, and the hook pad 30 is also sewn or attached to the end piece 72, providing an attached structure.

Figure 18:
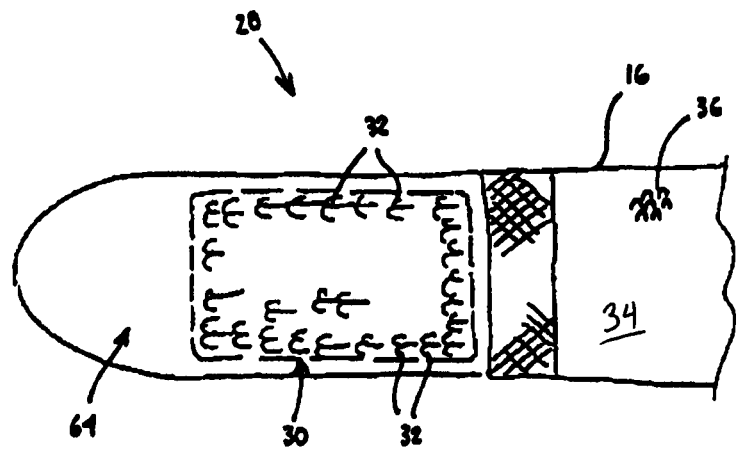
FIG. 18 is a plan view of another embodiment of a strap and attachment assembly for use in a mask mounting assembly according to the principles of the present invention.
Figure 19:
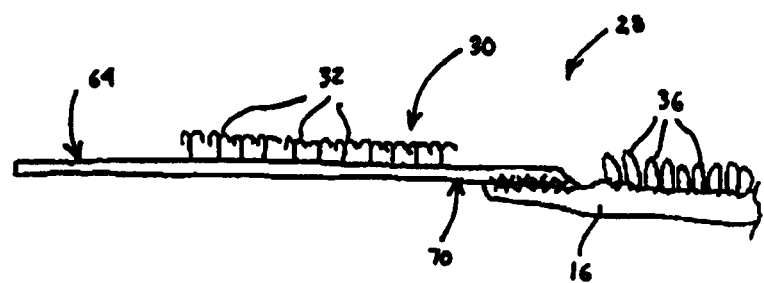
FIG. 19 is a side view of the strap and attachment assembly of FIG. 18.

Turning to the embodiment of FIGS. 18 and 19, the hook pad 30 is formed with the edge surface 64, as discussed above. Accordingly, only the bottom portion 70 of the hook pad 30 is sewn against the strap 16. Therefore, the embodiment of FIGS. 18 and 19 provides a two-piece structure.

Figure 20:
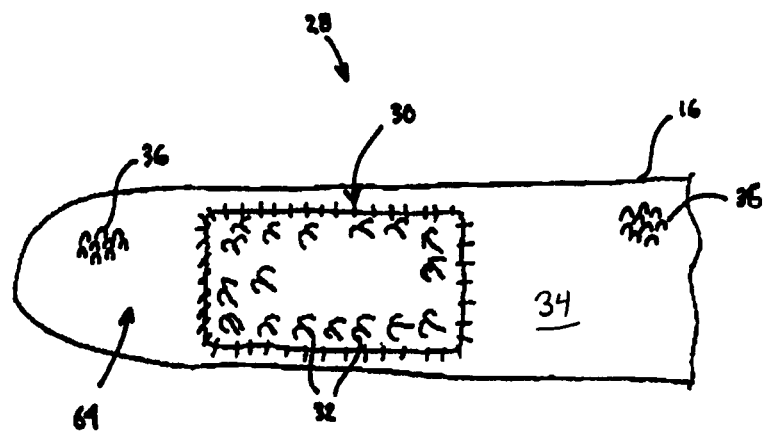
FIG. 20 is a plan view of a further embodiment of a strap and attachment assembly for use in a mask mounting assembly according to the principles of the present invention.
Figure 21:
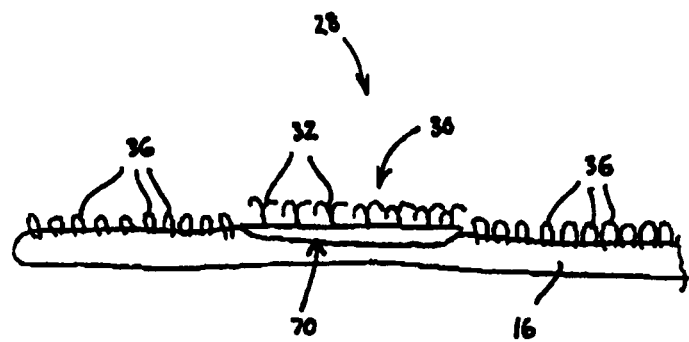
FIG. 21 is a side view of the strap and attachment assembly of FIG. 20.

In yet another embodiment, and as illustrated in FIGS. 20 and 21, the hook pad 30 is embedded within and sewn or otherwise attached to the surface 34 of the strap 16. In this embodiment, the edge surface 64 is a portion of the strap 16, which typically includes loops 36 for engaging the hooks 32. These loops 36 are formed as a soft material, as is known in the art, and therefore the edge surface 64 is a soft material that, if contacting the user's head A, does not provide any discomfort.

In this manner, the mask attachment assembly 10 provides a flexible and more comfortable attachment assembly, or headgear, for use in connection with a mask 102. Further, the present invention provides a mask attachment assembly 10 and patient interface device 100 that is more flexible and more easily positionable to satisfy the user's head A size and desired positions. Further, the present invention provides an easily releasable attachment assembly 18, 22, a quick-release assembly, such as through the release slot 118, and an easy positioning of the panel member 12 by sliding the strap 16 through the sleeves 14. In addition, the attachment assemblies 18, 22 allow for the easy removal of the strap 16 from the mask 102 or any component or subcomponent of the patient interface device 100. Accordingly, removal or disengagement of the attachment assembly 18, 22 (which are part of the straps 16) provides for the removal and/or release of the straps 16 from indirect attachment to the mask 102, the mask conduit coupling 120, the forehead support assembly 134 or any combination thereof.

Further, the mask attachment assembly 10 can be used in connection with a variety of attachment positions on the mask 102. For example, the mask attachment assembly 10 can be a two-point attachment assembly, a three-point attachment assembly, a four-point attachment assembly, etc. In this embodiment, at least one of the attachment points would be at the first engagement member 106, the second engagement member 110 and/or the engagement member 136.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A strap for use in a mask attachment assembly, comprising:
a hook pad provided on a first portion of a surface of the strap, the first portion being located at an end of the strap and forming a terminal end portion of the strap, the hook pad having a first width extending perpendicularly to a longitudinal axis of the strap from a first terminal side of the hook pad to a second terminal side of the hook pad opposite the first terminal side of the hook pad, the hook pad having a plurality of hooks extending entirely across the first width from the first terminal side to the second terminal side such that an entirety of the surface of the hook pad is covered by the hooks;
a plurality of loops provided on a second portion of the surface of the strap, the second portion having a second width extending perpendicularly to the longitudinal axis of the strap from a first terminal side of the strap at the second portion to a second terminal side of the strap at the second portion opposite the first terminal side, wherein the plurality of loops extend entirely across the second width from the first terminal side to the second terminal side such that an entirety of the surface of the strap at the second portion is covered by the loops, and wherein the plurality of loops are configured to engage the plurality of hooks in a releasable and engageable manner, wherein the second width is greater than the first width; and
an outer edge portion of the first portion of the surface surrounding at least a portion of the hook pad, wherein the outer edge portion does not include any hooks, wherein the first portion has a third width extending perpendicularly to the longitude axis of the strap from a first terminal side of the strap at the first portion to a second terminal side of the strap at the first portion, wherein the third width is greater than the second width.

2. The strap according to claim 1, wherein the first portion is immediately adjacent the second portion.

3. The strap according to claim 2, wherein the outer edge portion includes a second plurality of loops.

4. The strap according to claim 1, wherein the outer edge portion is formed from a coated material, a soft material, a padded material, a pliable material or any combination thereof.

5. A mask attachment assembly for use in attaching a mask in a sealed position on a user's face, the assembly comprising:
(a) a panel member having at least one sleeve extending along at least a portion of the panel member; and
(b) at least one strap extending through and slidable within the sleeve, the strap including:
(i) a first attachment assembly positioned on a first end of the strap and configured to engage a first engagement member positioned on a first side of the mask, and
(ii) a second attachment assembly positioned on a second end of the strap and configured to engage a second engagement member positioned on a second side of the mask, wherein the strap is repositionable by releasing the first attachment assembly or the second attachment assembly from the respective engagement member, and engaging the first attachment assembly or the second attachment assembly with the respective engagement member, wherein one of the first attachment assembly or the second attachment assembly is a hook-and-loop structure that, when engaged, forms a releasable contact surface, wherein the hook-and-loop structure comprises:

(1) a hook pad provided on a first portion of a surface of the strap, the first portion being located at an end of the strap and forming a terminal end portion of the strap, the hook pad having a first width extending perpendicularly to a longitudinal axis of the strap from a first terminal side of the hook pad to a second terminal side of the hook pad opposite the first terminal side of the hook pad, the hook pad having a plurality of hooks extending entirely across the first width from the first terminal side to the second terminal side such that an entirety of the surface of the hook pad is covered by the hooks, (2) a plurality of loops provided on a second portion of the surface of the strap, the second portion having a second width extending perpendicularly to the longitudinal axis of the strap from a first terminal side of the strap at the second portion to a second terminal side of the strap at the second portion opposite the first terminal side, wherein the plurality of loops extend entirely across the second width from the first terminal side to the second terminal side such that an entirety of the surface of the strap at the second portion is covered by the loops, and wherein the plurality of loops are configured to engage the plurality of hooks in a releasable and engageable manner, wherein the second width is greater than the first width, and (3) an outer edge portion of the first portion of the surface surrounding at least a portion of the hook pad, wherein the outer edge portion does not include any hooks, wherein the first portion has a third width extending perpendicularly to the longitudinal axis of the strap from a first terminal side of the strap at the first portion to a second terminal side of the strap at the first portion, wherein the third width is greater than the second width.

6. The mask attachment assembly according to claim 5, wherein the first portion is immediately adjacent the second portion.

7. The mask attachment assembly according to claim 6, wherein the outer edge portion includes a second plurality of loops.

8. The mask attachment assembly according to claim 5, wherein the outer edge portion is formed from a coated material, a soft material, a padded material, a pliable material or any combination thereof.

* * * * *